United States Patent [19]
Church

[11] Patent Number: 5,622,259
[45] Date of Patent: Apr. 22, 1997

[54] REDUCTION OF DISCOLORATION IN PLASTIC MATERIALS

[76] Inventor: Jonathan M. Church, Pfizer Inc. 235 E. 42nd St. 20th Floor, New York, N.Y. 10017-5755

[21] Appl. No.: 473,681

[22] Filed: Jun. 7, 1995

[51] Int. Cl.$^6$ ............................ B65D 85/30; B29C 71/04
[52] U.S. Cl. ..................... 206/363; 264/1.27; 264/1.38; 264/488; 204/901
[58] Field of Search ................................ 264/488, 489, 264/494, 446, 232, 340, 1.38, 1.27; 425/174.4; 204/901; 206/363

[56] References Cited

U.S. PATENT DOCUMENTS

| | | |
|---|---|---|
| 4,889,407 | 12/1989 | Markle et al. . |
| 5,098,618 | 3/1992 | Zelez ........................ 264/1.38 |
| 5,162,130 | 11/1992 | McLaughlin ............... 264/494 |
| 5,246,109 | 9/1993 | Marklet et al. . |
| 5,257,338 | 10/1993 | Markle . |

FOREIGN PATENT DOCUMENTS 3-52936  3/1991  Japan ........................ 264/446

OTHER PUBLICATIONS

M. F. Sturdevant, "How Sterilization Changes Long–Term Resin Properties", Plastics Engineering, Jan. 1991, pp. 27–32.

*Primary Examiner*—Mathieu D. Vargot
*Attorney, Agent, or Firm*—Peter C. Richardson; Lawrence C. Akers; Mark Dryer

[57] ABSTRACT

A method for reducing discoloration in a discolored plastic material which has been subjected to sterilization by gamma radiation which includes exposing the plastic material to light having a wavelength within the range of 200 to 600 nm for a time sufficient to restore the original clarity. A sterilized pack for a medical device including plastic material in which the clarity has been restored by the method is also included.

9 Claims, 1 Drawing Sheet

REDUCTION OF DISCOLORATION IN PLASTIC MATERIALS

FIELD OF THE INVENTION

This invention relates to a method for reducing discoloration in a plastic material. More particularly, the invention is concerned with the restoration of clarity in plastic materials which have been discolored by gamma irradiation. The invention also relates to a sterilized pack comprising or containing elements made of plastic material which has been sterilized by exposure to gamma radiation resulting in discoloration of at least some of the plastic material and wherein the original color or clarity of the plastic material has been restored.

BACKGROUND OF THE INVENTION

Many medical devices contain components made from a plastic material which initially may be white, colored or clear and transparent. Furthermore, medical devices are packaged in containers or envelopes which frequently are made of clear and transparent plastic material. If the device is to be used in a surgical procedure, particularly an invasive procedure, it must be sterilized before or after packaging and usually the whole pack comprising the container and device is sterilized.

The container of the pack is frequently made from a white or clear plastic material, or a combination of white and clear plastic and typical plastic materials are polyurethanes, polyvinylchloride (PVC), polyethylene, polyethylene terephthalate glycolate (PETG), polycarbonate and acrylic polymers, particularly polymethyl methacrylate (PMMA). A medical device of particular interest is an invasive sensor for the determination of analytes in blood and a typical component of such a sensor is transparent acrylic (e.g., PMMA) optical fiber.

U.S. Pat. No. 4,889,407 discloses an optical waveguide sensor in which a preferred waveguide is an optical fiber made from clear PMMA. Such a sensor may incorporate a device for returning light such as that disclosed in U.S. Pat. No. 5,257,338.

Sensors of the type disclosed in U.S. Pat. Nos. 4,889,407 and 5,257,338 are used in a multi-parameter sensor available under the Registered Trade Mark "Paratrend 7" from Biomedical Sensors Limited, High Wycombe, England.

A preferred package for the Paratrend 7 is disclosed in U.S. Pat. No. 5,246,109, which package comprises a number of components made from a plastic material, including a transparent blister pack made from PETG.

A number of sterilization techniques are known in the art and have been used to sterilize plastic-containing packs for surgical or medical procedures, for example, PVC blood bags and various tubing sets, as well as the sensor devices mentioned above. A common sterilization technique utilizes ethylene oxide as the sterilization medium. A disadvantage of this technique is that it takes some time, usually up to two weeks, before the amount of residual ethylene oxide drops to an acceptable level.

An alternative sterilization technique is irradiation by gamma radiation. This has the advantage that there is no contamination by the sterilizing agent. However, a disadvantage of the gamma irradiation technique is that many plastic materials, particularly clear, transparent plastic materials, become discolored by the gamma radiation.

Examples of such discoloration are that PVC turns a greeny brown, polycarbonate turns green, polyethylene yellows and acrylics turn an orangey brown.

Although, in many cases, the discoloration fades somewhat over time if the pack is maintained in the dark, the plastic material never recovers to its original color or clarity. Apart from being aesthetically undesirable, the discoloration may interfere with or reduce the efficiency of the article, particularly when the device is an optical fiber in which discoloration may affect the sensitivity of optical signals, or if the device is one in which clarity is necessary to monitor the state of material within the device, for example, a transparent Y-connector in a tube arrangement where, for example, bubbles in the liquid would not be visible if the transparent wall is badly discolored.

Accordingly, it is highly desirable that discoloration of plastic material in a medical device be reduced and, if possible, the material be restored to its original color to facilitate not only the appearance of the plastic material, but also the effectiveness of the device.

A study of the effect of sterilization, particularly using ethylene oxide or gamma radiation, on rigid thermoplastic resins was reported in an article by Marianne F. Sturdevant entitled "How Sterilization Changes Long-term Resin Properties", Plastics Engineering, January 1991, pages 27–32. The article is primarily concerned with the long-term effects, up to one year, of gamma radiation sterilization on the physical properties of plastic materials, especially styrenic polymers, such as styrene-acrylonitrile copolymer (SAN), general purpose polystyrene (GPPS), high-impact polystyrene (HIPS), and acrylonitrile-butadiene-styrene (ABS); polycarbonate (PC); linear low-density polyethylene (LLDPE) and rigid thermoplastic polyurethanes (RTPU).

The article discusses the effects of gamma radition on the optical properties of the plastic materials and mentions that all materials that were exposed to gamma radiation were discolored to varying degrees and that discoloration increased with increasing dosages. The article also stated that the initial discoloration diminished with time and that for PC and some of the styrene-based polymers exposure of the irradiated sample to mild UV light can accelerate the decrease in discoloration by a phenomenon known as photobleaching. However, since the investigation reported in the article was concerned primarily with changes in long term physical properties, such as tensile strength and impact resistance, and the photo-bleaching effect was "solely an optical phenomenon", the reduction of discoloration was not seriously pursued and it was not recognized that the original clarity and lustre of clear and transparent plastic material could be completely restored by controlled irradiation with "blue light" as described hereinafter.

Surprisingly, it has now been found that discoloration induced by gamma radiation sterilization may be substantially diminished and the original color and clarity of the material be substantially restored by exposing the discolored material to electromagnetic radiation having a wavelength within the range of 200 to 600 nm, particularly blue light having a maximum wavelength of 420 nm, for a period of time of less than twenty four hours.

A sterilized pack, such as that disclosed in U.S. Pat. No. 5,246,109, in which discoloration produced by gamma radiation sterilization is removed by the technique disclosed herein, is also within the scope of the present invention.

Electromagnetic radiation having a wavelength within the stated range of 200 to 600 nm is partly within the ultraviolet region of the electromagnetic spectrum, i.e., up to about 390 nm is ultraviolet radiation, and partly within the visible light portion of the spectrum, i.e., from about 390 to 600 nm. The preferred radiation having a peak wavelength of about 420 nm is in the violet or far-blue portion of the spectrum and is herein designated as "blue light". For convenience, and also to clearly distinguish from the gamma radiation mentioned herein, the radiation used in the method of the present invention, both in the ultraviolet and visible light regions of the electromagnetic radiation spectrum, is referred to as "light" having a wavelength within the range of 200 to 600 nm.

SUMMARY OF INVENTION

In accordance with the present invention there is provided a method for reducing discoloration in a discolored plastic material having an unacceptable level of discoloration, which method comprises placing the material in a closed chamber containing at least one lamp which produces light having a wavelength within the range of 200 to 600 nm, and exposing the material to said light for a time sufficient to reduce the discoloration in the plastic material to an acceptable level.

In carrying out the method of the invention, a suitable time of exposure, depending upon the intensity of the light and the nature of the plastic material, is from twelve to twenty four hours, preferably about sixteen hours.

In a preferred embodiment of the invention, plastic material in which discoloration is produced by sterilizing with gamma radiation is treated according to the method of the invention and the exposure to light is conducted until the plastic material is substantially restored to its original appearance. In many cases, it has been found that treatment according to the method of the invention results in a material which is even more lustrous than the original material.

Preferably, the source of light is one or more linear fluorescent lamps, each having a power of 120 watts and narrow band emission peaking at a wavelength of about 420 nm, with maximum output when the temperature of the coldest part of the lamp is about 40° to 50° C.

In a particularly preferred embodiment, the method is carried out with from six to twelve of the stated fluorescent lamps mounted in an air-cooled cabinet, having stainless steel walls. The cooling is carried out by forced air flow over the lamps in order to maintain the temperature within the cabinet at an optimum for maximum output of the lamps. The stainless steel walls provide reflecting surfaces within the cabinet to maintain an efficient intensity of light and thereby reduce the treatment time.

The invention also provides a sterilized pack for a medical device which comprises an envelope of transparent plastic material accommodating a device, at least part of which is made of plastic material, which pack has been sterilized by gamma radiation resulting in discoloration of at least some of the plastic material, wherein the original clarity of said plastic material is restored by exposing the pack to light having a wavelength within the range of 200 to 600 nm.

A preferred pack according to the invention is one in which the envelope is made from transparent polyethylene terephthalate glycolate and the devie comprises at least one optical fiber made from transparent polymethyl methacrylate.

The method of the present invention is particularly suitable for restoring the original clarity to plastic material which is present in or forms part of a medical device which has been sterilized with gamma radiation. Such material includes acrylic plastic material, particularly PMMA optical fiber, and also clear transparent PETG which is used for at least part of the packaging of a medical device.

When the device comprising at least one PMMA optical fiber and the packaging made from PETG is sterilized with gamma radiation, usually about 2.5 to 10 megarads, the plastic material is discolored and the device can not be used until the discoloration is dissipated, which, prior to the present invention, was achieved by storing the device in the dark for an extended period, usually about one week at 55° C., and even then, the original clarity was not completely restored.

By treating the plastic material with the method of the present invention the discoloration may be reduced and the original clarity substantially restored.

DESCRIPTION OF THE DRAWINGS

A preferred embodiment of an apparatus for performing the method is illustrated in the accompanying drawings, in which.

DETAILED DESCRIPTION OF THE INVENTION

Figure 1:
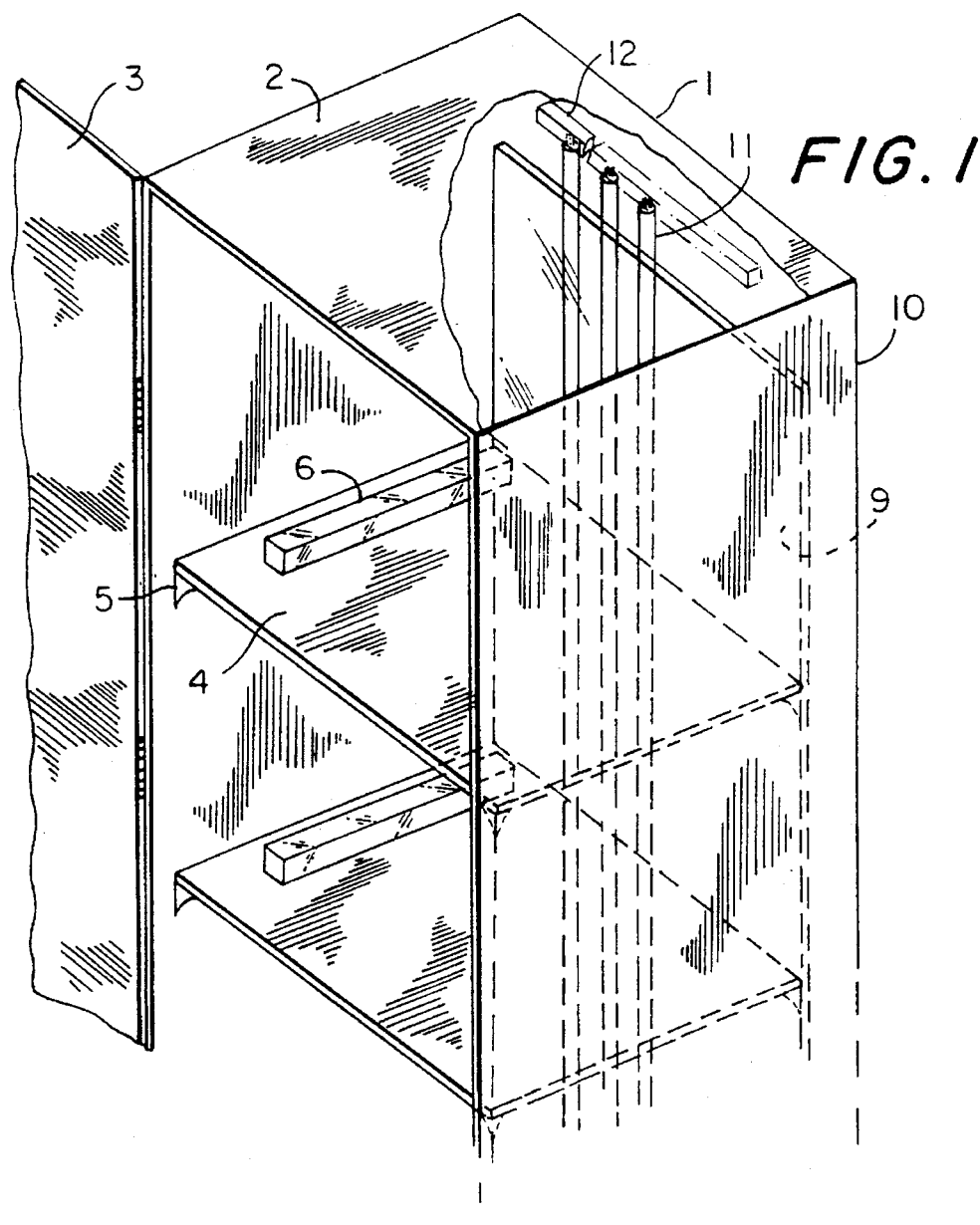
FIG. 1 is a partial perspective view of a lighting cabinet embodying the apparatus.
Figure 2:
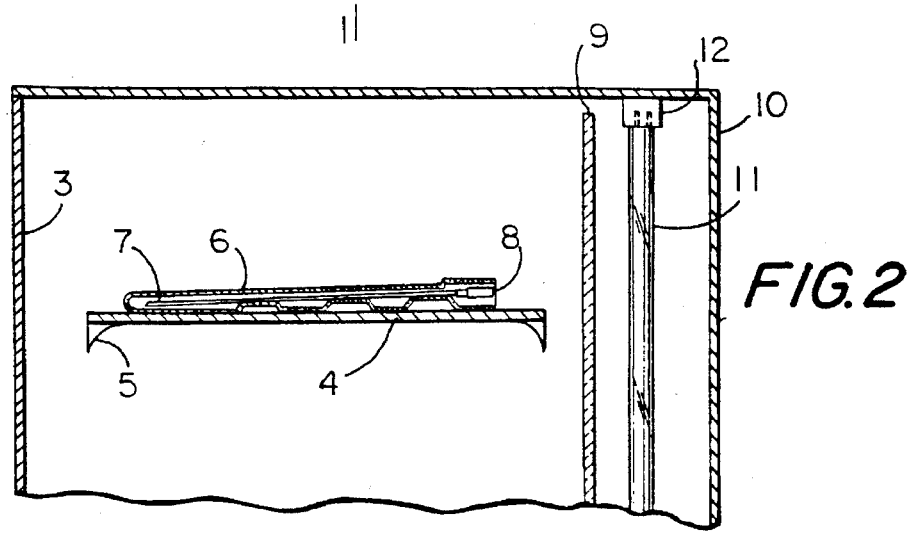
FIG. 2 a side sectional elevation of a rack within the cabinet of FIG. 1.

The preferred apparatus for carrying out the method of the invention, as illustrated in the drawings, comprises a cabinet 1 having walls made of stainless steel, the internal surfaces 2 of which have high reflectance. The front of the cabinet is closed by a hinged door 3. Mounted within the cabinet are a number of horizontal trays 4. The trays are mounted on adjustable brackets 5, so that the number and spacing of the trays may be varied according to the size and number of the articles to be treated. In FIG. 1 two trays are shown, but for medical devices, as exemplified herein, six or more trays may be used. Each tray may hold a number of packaged devices 6 and a typical tray in the preferred embodiment usually holds forty two packs. In the embodiment illustrated, each pack 6 comprises a blister pack of clear transparent PETG containing a sensor 7 (see FIG. 2) comprising one or more, usually three, optical fibers made from PMMA and terminating at the proximal end in an electro-optical connector 8. A plurality of the packs, usually forty two, are stacked side by side (Only one is shown in each tray in FIG. 1) with their proximal ends facing a transparent glass window 9 mounted vertically at the back of the cabinet. Behind the glass window and between the window and the rear wall of the cabinet 10 is mounted a plurality of linear fluorescent lamps 11. The lamps are mounted vertically and are held at each end in a standard electrical socket 12. The preferred embodiment contains twelve fluorescent lamps, each having a length of 150 cm., a diameter of about 3.8 cm., a power of 120 watts and a narrow band emission peaking at a wavelength of about 420 nm with maximum output when the temperature of the coldest part of the lamp is about 40° to 50° C. The optimum working temperature for the lamps is maintained by air cooling of the cabinet (not shown).

When packs containing medical devices, such as the sensors described above, are sterilized with gamma radiation and the plastic material in the pack becomes discolored, the original color and clarity are substantially restored by placing the packs in the trays of the cabinet as described above and exposing them to the "blue light" emitted by the fluorescent lamps for a period of up to twenty four hours. With the preferred embodiment particularly described above, exposure of only about sixteen hours is usually sufficient to completely restore the original clarity and lustre of the plastic material.

I claim:

1. A method for reducing discoloration in a discolored plastic material in which the discoloration was produced by sterilizing the plastic material with gamma radiation, which method comprises placing the material in a closed chamber containing at least one lamp which produces light having a wavelength within the range of 200 to 600 nm and exposing the material to said light for up to twenty four hours to reduce the discoloration in the plastic material until the material is substantially restored to its original appearance.

2. A method according to claim 1 in which the time of exposure is from twelve to twenty four hours.

3. A method according to claim 1, in which the source of light is one or more linear fluorescent lamps, each having a power of 120 watts and a narrow band emission peaking at a wavelength of about 420 nm with maximum output when the temperature of the coldest part of the lamp is about 40° to 50° C.

4. A method according to claim 3, in which the source of light is six to twelve of the said lamps mounted in an air-cooled cabinet having stainless steel walls.

5. A method according to claim 1, in which the plastic material is originally a clear transparent acrylic plastic material which has been discolored after being irradiated with gamma radiation and in which the original clarity is restored by subjecting the material to light having a peak wavelength maximum of 420 nm for a period of from twelve to twenty four hours.

6. A method according to claim 5, in which the material is in the form of a polymethyl methacrylate optical fibre.

7. A method according to claim 1, in which the plastic material is in the form of a container for a medical device at least one wall of which is made from a polycarbonate or clear transparent polyethylene terephthalate glycolate.

8. A sterilized pack for a medical device which comprises an envelope of transparent plastic material accommodating a device, at least part of which is made of plastic material, which pack has been sterilized by gamma radiation resulting in discoloration of at least some of the plastic material, wherein the original clarity of said plastic material is restored by exposing the pack to light having a wavelength within the range of 200 to 600 nm for a time up to twenty four hours to restore the original clarity.

9. A pack according to claim 8, in which the envelope is made from transparent polyethylene terephthalate glycolate and the device comprises at least one optical fiber made from polymethyl methacrylate.

* * * * *